(12) United States Patent
Finger et al.

(10) Patent No.: US 11,406,843 B2
(45) Date of Patent: *Aug. 9, 2022

(54) POLYMERIC RADIATION-SOURCES

(71) Applicant: IP LIBERTY VISION CORPORATION, Suite, NY (US)

(72) Inventors: Paul T. Finger, New York, NY (US); Toby Welles, New York, NY (US); Jaime Simon, New York, NY (US)

(73) Assignee: IP LIBERTY VISION CORPORATION, New York, NY (US)

( * ) Notice: Subject to any disclaimer, the term of this patent is extended or adjusted under 35 U.S.C. 154(b) by 191 days.

This patent is subject to a terminal disclaimer.

(21) Appl. No.: 16/543,573

(22) Filed: Aug. 18, 2019

(65) Prior Publication Data
US 2020/0086141 A1 Mar. 19, 2020

Related U.S. Application Data

(63) Continuation of application No. 14/243,703, filed on Apr. 2, 2014, now Pat. No. 10,384,078.

(51) Int. Cl.
| | |
|---|---|
| *A61N 5/10* | (2006.01) |
| *A61K 51/06* | (2006.01) |
| *C08K 5/42* | (2006.01) |
| *C08G 18/83* | (2006.01) |
| *C08F 10/02* | (2006.01) |
| *C08G 18/32* | (2006.01) |
| *C08G 18/76* | (2006.01) |
| *C08G 18/82* | (2006.01) |
| *C08G 64/10* | (2006.01) |
| *C08G 64/24* | (2006.01) |

(52) U.S. Cl.
CPC .......... *A61N 5/1028* (2013.01); *A61K 51/065* (2013.01); *A61N 5/1001* (2013.01); *A61N 5/1017* (2013.01); *C08F 10/02* (2013.01); *C08G 18/3206* (2013.01); *C08G 18/7657* (2013.01); *C08G 18/82* (2013.01); *C08G 18/833* (2013.01); *C08G 64/10* (2013.01); *C08G 64/24* (2013.01); *C08K 5/42* (2013.01); *A61N 2005/1019* (2013.01); *A61N 2005/1094* (2013.01)

(58) Field of Classification Search
CPC ................ A61N 5/1001; A61N 5/1002; A61N 5/1014–1017; A61N 5/1019; A61N 5/1021; A61N 5/1023–1025; A61N 5/1027–1029; A61K 51/0406
See application file for complete search history.

(56) References Cited

U.S. PATENT DOCUMENTS

| | | | | |
|---|---|---|---|---|
| 5,621,780 | A * | 4/1997 | Smith | G21K 5/04 378/65 |
| 6,248,057 | B1 * | 6/2001 | Mavity | A61N 5/1027 600/3 |
| 2003/0204125 | A1 * | 10/2003 | Brauckman | A61N 5/1027 600/3 |

(Continued)

*Primary Examiner* — Carrie R Dorna
(74) *Attorney, Agent, or Firm* — Smith Tempel; Steven P. Wigmore

(57) ABSTRACT

A polymeric radiation-source with customized geometries to maximize receipt of radiation into treatment areas that is formed from either radioisotopes molecularly bonded to a polymer or radioisotopes encased within a polymer.

20 Claims, 4 Drawing Sheets

(56) References Cited

U.S. PATENT DOCUMENTS

2006/0067467 A1* 3/2006 Chornenky .......... A61N 5/1015
378/65
2011/0201866 A1* 8/2011 Cipriani ................ A61P 35/00
600/1

* cited by examiner

POLYMERIC RADIATION-SOURCES

CROSS REFERENCE TO RELATED APPLICATIONS

This application claims the benefit of U.S. Ser. No. 61/891,361, filed on Oct. 15, 2013, which is incorporated by reference herein in its entirety.

FIELD AND BACKGROUND OF THE INVENTION

The present invention generally relates to relates to polymeric radiation-sources with customized geometries for enhanced radiation administration into treatment volumes of various sizes, surface geometries, and shapes.

BRIEF DESCRIPTION OF THE DRAWINGS

The subject matter regarded as the invention is particularly pointed out and distinctly claimed in the concluding portion of the specification. The invention, in regards to its features, components and their configuration, operation, and advantages are best understood with reference to the following description and accompanying drawings in which:

DETAILED DESCRIPTION OF EMBODIMENTS OF THE PRESENT INVENTION

In the following detailed description, numerous details are set forth in order to provide a thorough understanding of the invention. However, it will be understood by those skilled in the art that the present invention may be practiced without these specific details and that well-known methods, procedures, and components have not been described in detail so as not to obscure the present invention.

Embodiments of the present invention are generally directed to an ophthalmic radiation device and, specifically, to embodiments of a radioactive-source material used in the device.

The following terms will be used out through the document:

"Radioactive source material", "source", "source material", "radioactive source", radioisotope all refer to a emitters of any one or a combination of, inter alia, alpha particles, beta particles, positrons, Auger electrons, gamma-rays, or x-rays.

"Polymeric radiation source" refers to either a polymer molecularly bonded to a radioisotope or polymeric encasement of radioisotopes.

"Polymer" refers to a molecule formed from repetitive monomers; whether carbon based or non-carbon based.

"DTPA"—refers to diethylenetriaminepentaacetic acid

"Proximity" or "close proximity" refer to a distance between a radiation-source and a surface of a treatment volume into which a therapeutic or otherwise beneficial dose of radiation radiates.

"Surface geometry" refers to the angularity of the surface.

"Shape" refers to the contour or the outer boundary of an object.

"Treatment area" refers to either a biological or a non-biological area to which the radiation is targeted. The treatment area is typically the interface between the polymeric, radiation-source and the treatment volume.

Without diminishing in scope, a polymeric radiation source will be discussed also in terms of a disk of radioactive epoxy.

Figure 1:
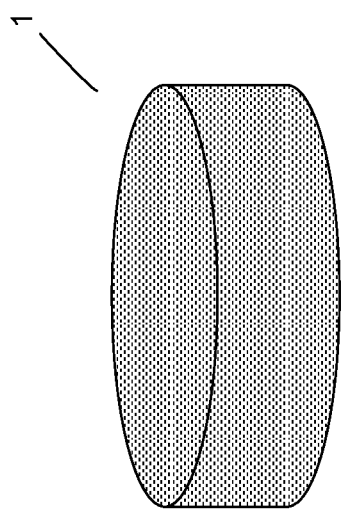
FIG. 1 is a schematic, perspective view of a disk of a radioisotope molecularly bonded to a polymer, according to an embodiment.

Turning now to the figures, FIG. 1 depicts a generally cylindrical, polymeric radiation-source 1 or disk having a thickness of approximately 1.0 mm thick and diameter between about 2.0 mm to 22.0 mm. It should be appreciated that polymeric radiation source 1 can be formed into symmetrical or asymmetrical shapes of assorted surface geometries so as to modulate the radiation field in accordance with a particular need.

During manufacture of the source from radioactive epoxy, image data of a treatment area can be derived from data provided by three dimensional medical imaging techniques like, inter alia Magnetic Resonance Imaging (MRI), Three-Dimensional Ultrasound, Computed Axial Tomography (CAT or CT), Single-Photon Emission Computed Tomography (SPECT) or Positron Emission Tomography (PET), for example.

The image includes both surface geometry and shape data that can be used in a variety of manufacturing processes like, inter alia cutting, three-dimensional printing, or other rapid prototyping techniques like laser sintering, stereolithography, or fused filament fabrication. It should be appreciated that in a certain embodiment, these processes may be used to produce a mold for casting or forming of the polymeric radiation-source 1.

In a certain embodiment, a radioactive polymer, from which the polymeric radiation-source 1 is formed, is produced by making a complex of a radioisotope and a bi-functional ligand and combining the complex with a polymer. When using metallic radioisotope, the bi-functional ligand is implemented as a bi-functional chelating agent in which a chelant functional group bonds to the metal radioisotope and a second functional group bonds to the polymer.

Following is a sample method of producing a radioactive polymer and each of the test steps involved.

A suitable epoxy component like D.E.R.™ 331™ and suitable epoxy curing component like JEFFAMINE® D-230 Polyetheramine were acquired from epoxy distributors; their structures are shown below:

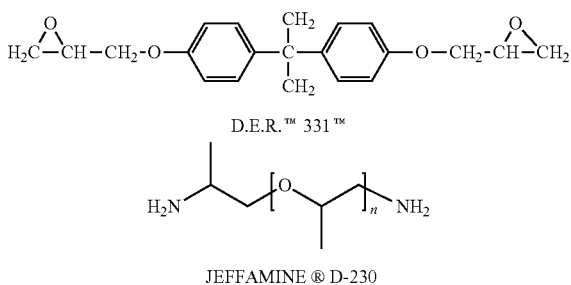

D.E.R.™ 331™

JEFFAMINE ® D-230

In order to examine the ability to prepare the epoxy parts without metals, formulations were prepared in 5 cm aluminum cups. The formula included adding 3.8 g of D.E.R.™ 331™ to the cup followed by the addition of 1.8 g of the amine. The two were stirred until mixed then heated in an oven at 75.degree. C. for two hours. The parts were heated overnight in the same oven at 75.degree. C. and showed no visual deformities.

In order to examine the ability to prepare parts with metals, a new mixture was prepared and metals were added to the mixture one with commercially available chelating agents and another without chelating agents. The two chelating agents selected included acetylacetone (AcAc) and a DOTA based bi-functional chelating agent (BFC). Acetylacetone was selected because it enhances the ability of metals to be incorporated into epoxy resins. The bi-functional chelating agent was chosen because it would make a neutral chelate with Y-90 and have an amine functional group that would react with the epoxy resin; the structures are shown below:

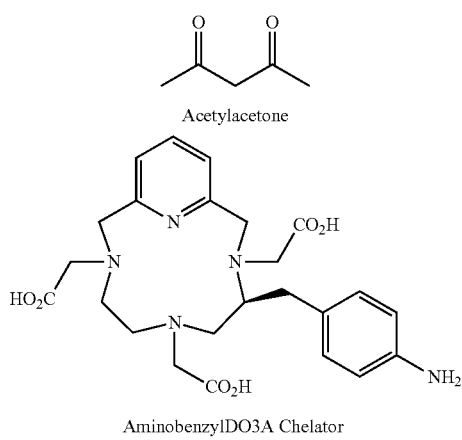

Acetylacetone

AminobenzylDO3A Chelator

When chelating agents were used, the metal was placed in a vial and chelating agent was added. The pH was adjusted to above 9. The part was prepared by adding 1.8 g of epoxy to the aluminum cup then adding the chelate solution and mixing. This was followed by adding 3.8 g of D.E.R.™ 331™ and stirring then heating at 75.degree. C. for two hours.

Non-radioactive metal experiments were performed using 100 uL of 0.2 M yttrium solution. This was about 10 times what would need for 160 uCi. When yttrium with the amine were mixed without adding chelating agent, white turbidity appeared upon stirring and persisted even after adding D.E.R™ 331™; but, turned clear upon curing the resin. 20 mg of acetylacetone which accounts for 5 times the amount of yttrium resulted in a clear solution when the amine was added. After heating the final part remained clear. There did not seem to be a pH adjustment needed when using acetylacetone.

When using five times the amount of DOTA-based chelating-agent, the mixture of amine was clear only when pH was adjusted prior to mixing. The turbidity of the materials when the pH was not adjusted thus implied that no chelate was formed until the pH was adjusted.

Afterwards tracer experiments were performed. Radioactive Lu-177 used to mimic Y-90 was purchased from Perkin Elmer. These two metals have a +3 charge and exhibit rare earth chemistry. Lu-177 has a longer half-life (6.73 days) and a gamma photon that can be used to trace the fate of the isotope. Ten mCi of Lu-177 in 5 uL of 0.5 M HCl was received. A volume of 95 uL of 0.5M HCl was added to make the solution 100 uCi/uL. One uL of Lu-177 per experiment was used.

Two separate parts, one containing no chelating agent and another containing 25 uL of acetylacetone were made. Both were cured at 75.degree. C. to hard colorless material. After curing the parts were rubbed with a paper towel to determine if there was any removable contamination. Small amounts of radioactivity (<0.1%) were removable from the surface and additional rubbing resulted in no activity loss. An additional 0.5 grams of resin (a 10% coating) was added to cover the acetylacetone part. The puck was cured as before and the rubbing test was performed again. This showed no activity. Thus a second layer of epoxy was enough to prevent removable activity upon rubbing. The two parts were imaged using a collimator and a phosphor imager to determine the homogeneity of the activity. The results showed the activity evenly distributed in both pucks as shown in FIG. 3D.

Three additional pucks were prepared using tracer amounts of Lu-177 (100 uCi) and carrier added yttrium (enough to mimic 10.times. for a 160 uCi of Y-90).

The pucks were formed with the changes in chelating agent: No chelating agent used. Acetylacetone used. DO3A based chelator (BFC) used.

They were prepared as described above and evaluated by for removable activity using a rubbing test. The results of the rubbing test are given below in percent of radioactivity removed:

| Puck Label (FIG. 1B) | Puck | First Rub | Second Rub | Third Rub |
| --- | --- | --- | --- | --- |
| 1a | No Chelant | 0.004 | 0.001 | 0.0005 |
| 1b | AcAc | 0.003 | 0.0005 | None |
| 1c | BFC | 0.001 | 0.0007 | 0.0004 |

Figure 1B:
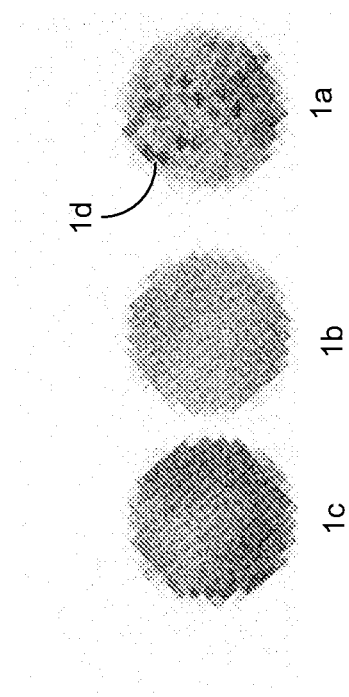
FIG. 1B are images of activity detected from experimental pucks containing Lu-177 and carrier added yttrium obtained by an imager during a carrier added experiment.
Figure 1A:
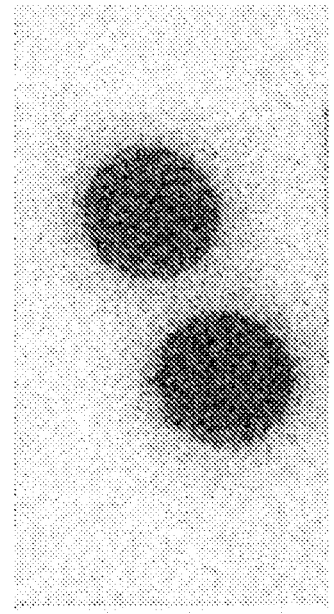
FIG. 1A depicts images of activity detected from experimental pucks containing Lu-177 obtained with phosphor imager during a tracer experiment.

The imaging results for pucks 1a-1c appear in FIG. 1B. Puck 1a exhibits isolated pockets of activity 1d whereas pucks 1b-1c depict homogenous activity.

Metallic radioisotopes that may be chelated with a bi-functional chelating agent include, inter alia, inter alia, $^{89}$Sr, $^{169}$Yb, $^{90}$Y, $^{192}$Ir, $^{103}$Pd, $^{177}$Lu, $^{149}$Pm, $^{140}$La, $^{153}$Sm, $^{186}$Re, $^{188}$Re, $^{166}$Ho, $^{166}$Dy, $^{137}$Cs, $^{57}$Co, $^{169}$Er, $^{165}$Dy, $^{97}$Ru, $^{193m}$Pt, $^{195m}$Pt, $^{105}$Rh, $^{68}$Ni, $^{67}$Cu, $^{64}$Cu, $^{109}$Cd, $^{111}$Ag, $^{198}$Au, $^{199}$Au, $^{201}$Tl, $^{175}$Yb, $^{47}$Sc, $^{159}$Gd, and $^{212}$Bi.

Following are additional examples of methods in which various types of radioisotopes may be bonded to various types of polymers. As noted above, embodiments of the radioactive polymer employ a bi-functional molecule capable of bonding with a radioisotope and also a polymer. If the radioisotope is a metal, it can be attached via a chelating group; but if it is not covalent attachment to the radioisotope can be employed.

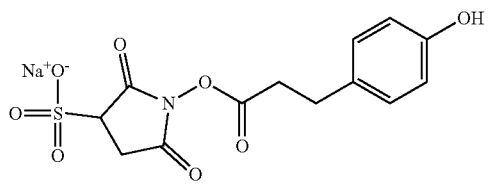

Water-Soluble Bolton-Hunter Reagent

For example, this molecule can be first reacted with iodine (e.g. 1-131) and an oxidizing agent such as chloramine-T or Iodogen to attach radioactive iodine to the phenol moiety. The left hand side has a reactive group that will react with amines to form amide linkages.

Polymer Example 1: Polyurethane

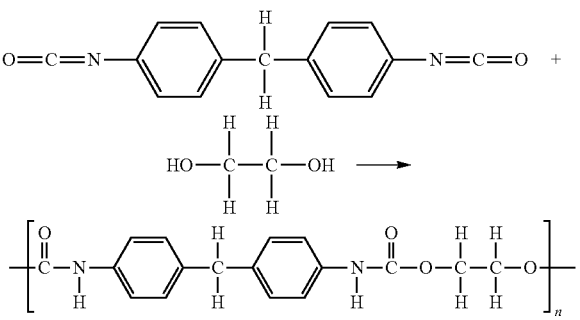

A glycol having a chelant functionality attached and a radioactive metal which has been attached to the chelant functionality, reacts with the polyurethane matrix to chemically bond the metallic radioisotope to the polymer. If the glycol has a phenolic group on it, it can be reacted with radioactive iodine, then incorporated into the polyurethane in the same way. It should be appreciated that the radioisotope can also incorporate on the isocyanate portion of a polymer.

Polymer Example 2: Polycarbonate

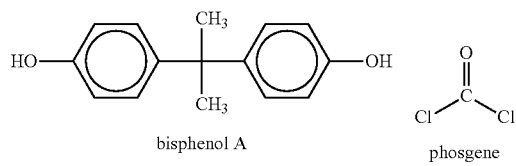

bisphenol A          phosgene

The monomers are bisphenol A and phosgene; the phenol functional groups can be iodinated with radioactive iodine before the reaction with phosgene to form radio-iodinated polycarbonate. Similarly, for metallic radioisotopes, one can modify some of the bisphenol A molecules with a chelating agent having bonded metallic radioisotopes to attach radioactive metals to the polycarbonate.

Polymer Example 3: Polyethylene

A reactive monomer is prepared with an unsaturated end and a chelant or a phenol on the other side. React the monomer with the radioisotope first then incorporate it into a small amount of polymer that could be blended into the polymer.

It should be appreciated that the above-described methodology can be used to bond radioisotopes to a various types of polymers like, inter alia, polycarbonates as noted above, polyesters, and epoxies.

$^{32}$P, $^{33}$P, and $^{77}$As may also be bonded to polymers in accordance to the general procedure described above.

Metallic radioisotopes that may be chelated with a bi-functional chelating agent include, inter alia, inter alia, inter alia, $^{89}$Sr, $^{169}$Yb, $^{90}$Y, $^{192}$Ir, $^{103}$Pd, $^{177}$Lu, $^{149}$Pm, $^{140}$La, $^{153}$Sm, $^{186}$Re, $^{188}$Re, $^{166}$Ho, $^{166}$Dy, $^{137}$Cs, $^{57}$Co, $^{169}$Er, $^{165}$Dy, $^{97}$Ru, $^{193m}$Pt, $^{195m}$Pt, $^{105}$Rh, $^{68}$Ni, $^{67}$Cu, $^{64}$Cu, $^{109}$Cd, $^{111}$Ag, $^{198}$Au, $^{199}$Au, $^{201}$Tl, $^{175}$Yb, $^{47}$Sc, $^{159}$Gd, and $^{212}$Bi.

$^{32}$P, $^{33}$P, and $^{77}$As may also be bonded to polymers in accordance to the general procedure described above.

Figure 2:
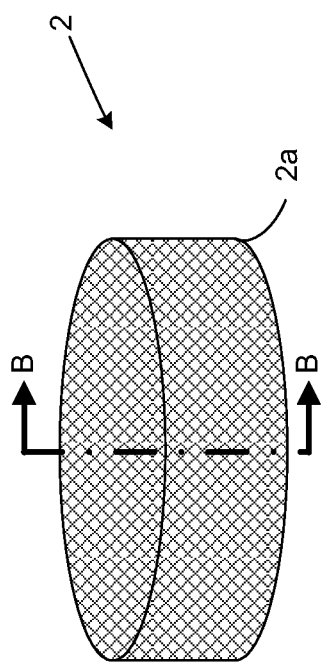
FIG. 2 is a schematic, perspective view of a polymeric radiation-source implemented as a radioisotope encased in a polymeric, disk-shaped encasement, according to an embodiment.

FIG. 2 is a perspective view of a polymeric radiation-source implemented as a non-radioactive polymeric encasement of radioisotopes. Polymeric encasement 2a is formed by any one or a combination of manufacturing processes including, inter alia, lamination, casting, drawing, forming, molding, blowing, adhesion, or extrusion. In certain embodiments, encasement 2a may also be constructed from a radiation-permeable me Hie or glass material to advantageously contain ablation, fragmentation, detachment, degradation, and selective attenuation of radiation emission.

Figure 4:
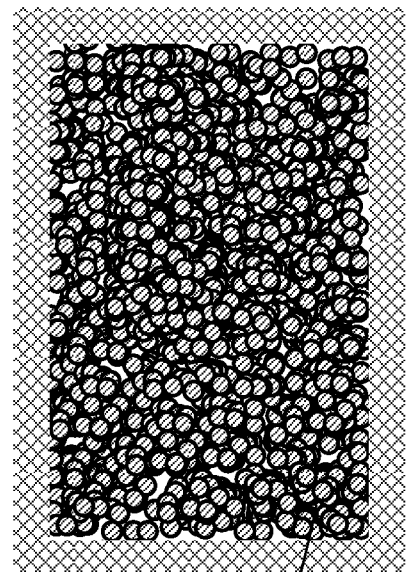
FIG. 4 is a schematic, cross-sectional view of the polymeric radiation-source of FIG. 2 depicting neutron-activated, glass microspheres encased in a polymeric encasement, according to an embodiment.
Figure 3:
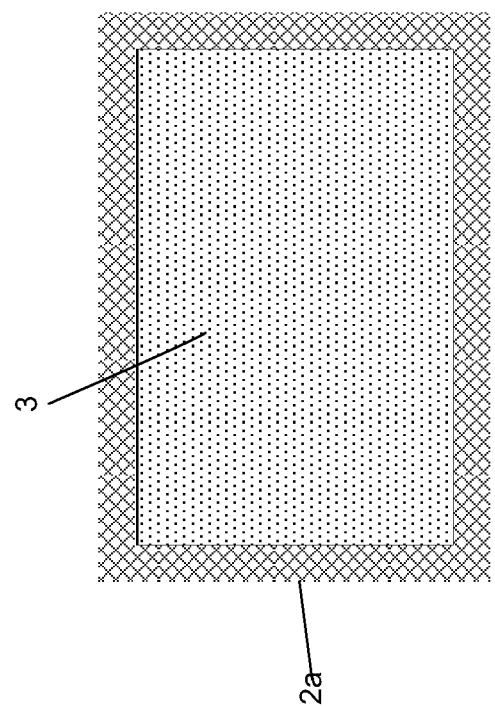
FIG. 3 is a schematic, cross-sectional view of the polymeric radiation-source of FIG. 2 depicting a radioisotope encased in a polymeric encasement, according to an embodiment.

FIGS. 3-4 are cross-sectional views along section line B-B of various embodiments of the polymeric radiation source 2 shown in FIG. 2.

Specifically, FIG. 3 depicts an embodiment of particulate or non-particulate radioisotope 3 encased inside epoxy encasement 2a. Radioisotope 3 may be selected from any one or a combination of, inter alia, $^{89}$Sr, $^{90}$Sr, $^{169}$Yb, $^{32}$P, $^{33}$P, $^{90}$Y, $^{192}$Ir, $^{125}$I, $^{131}$I, $^{103}$Pd, $^{177}$Lu, $^{149}$Pm, $^{140}$La, $^{153}$Sm, $^{186}$Re, $^{188}$Re, $^{166}$Ho, $^{166}$Dy, $^{137}$Cs, $^{57}$Co, $^{169}$Er, $^{165}$Dy, $^{97}$Ru, $^{193m}$Pt, $^{195m}$Pt, $^{105}$Rh, $^{68}$Ni, $^{67}$Cu, $^{64}$Cu, $^{109}$Cd, $^{111}$Ag, $^{198}$Au, $^{199}$Au, $^{201}$Tl, $^{175}$Yb, $^{47}$Sc, $^{159}$Gd, and $^{212}$Bi and $^{77}$As.

In certain embodiments, radioisotope 3 is implemented as an emitter of one or any combination of alpha particles, beta minus and beta plus particles, positrons, Auger electrons, gamma-rays, or x-rays.

Auger emitters include radioisotopes like, inter alia, $^{67}$Ga, $^{99m}$Tc, $^{111}$In, $^{123}$I, $^{125}$I, and $^{201}$Tl.

Alpha-emitters include radioisotopes like, inter alia, uranium, thorium, actinium, and radium, and the transuranic elements.

The choice of the particular radioisotope is determined by the particular therapeutic requirements.

FIG. 4 depicts an embodiment of polymeric, radiation-source 2 of FIG. 2 in which radioactive microspheres 4 of neutron-activated glass are encased inside epoxy encasement 2a.

Radioactive microspheres 4 have an average diameter ranging between about 0.2-10.0 microns from the materials noted above, according to an embodiment.

In certain embodiments, radioisotopes microspheres 4 are formed from glass-forming materials activated through bombardment with high-energy particles like neutrons; typically in a in a cyclotron. Such materials include, inter alia, yttrium aluminosilicate, magnesium aluminosilicate, holmium-166, erbium-169, dysprosium-165, rhenium-186, rhenium-188, yttrium-90, or other elements on the periodic table.

In certain other embodiments, radioisotopes microspheres 4 are formed from a mixture of glass forming materials and a radioisotope.

Glass forming materials include, inter alia, silica aluminum oxide, boric oxide, barium oxide, calcium oxide, potassium oxide, lithium oxide, magnesium oxide, sodium oxide, lead oxide, tin oxide, strontium oxide, zinc oxide, titanium dioxide, and zirconium oxide.

Examples of radioactive materials that may be mixed together with the glass forming materials include, inter alia, iodine-125, palladium-103, and strontium-90 to emit low energy gamma rays.

Figure 5:
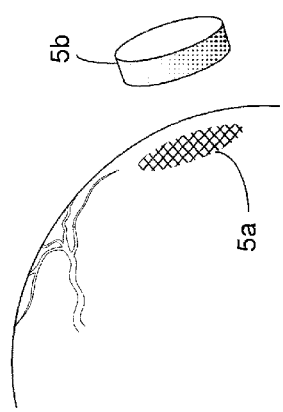
FIG. 5 is a schematic view of a polymeric, radiation-source having a symmetrical surface geometry substantially corresponding to that of a treatment area, according to an embodiment.

FIG. 5 depicts a custom-formed, polymeric radiation-source 5 having a circular shaped face with a flat surface geometry substantially corresponding to the surface area of treatment area 5a, according to an embodiment. In brachytherapy, polymeric radiation-source 5 is brought into proximity to diseased tissue 5a usually temporarily, as is known in the art.

Figure 6:
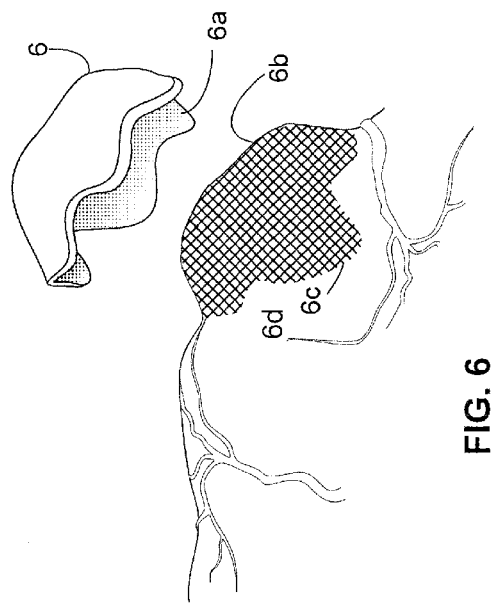
FIG. 6 is a schematic view of a polymeric, radiation-source having a three dimensional surface geometry and an irregular shape substantially corresponding to that of a treatment area, according to an embodiment.

FIG. 6 depicts a customized, polymeric radiation-source 6 for an irregular, three-dimensional treatment area 6b. As shown, customized, polymeric radiation-source 6 has a corresponding sloping surface geometry 6a to facilitate placement in maximum proximity to treatment area 6b and a substantially matching shape to facilitate alignment with contoured or protruding treatment areas 6c and to minimize radiation of healthy tissue 6d, according to an embodiment.

Figure 7:
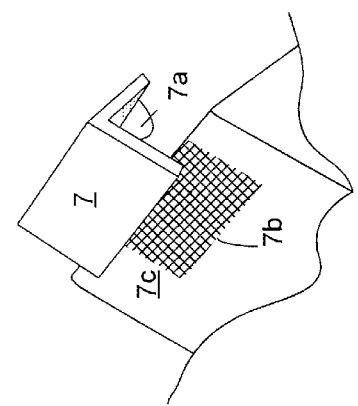
FIG. 7 is a schematic view of a polymeric, radiation-source having an angular surface geometry to facilitate an angular treatment area, according to an embodiment.

FIG. 7 depicts a customized polymeric, radiation-source 7 having an angular surface geometry 7a so as to facilitate placement in maximum proximity to treatment area 7b and also a substantially matching shape to facilitate alignment with, or fit with the boundaries of, the treatment area 7b while minimizing radiation to non-treatment area 7c, as noted above.

Figure 8:
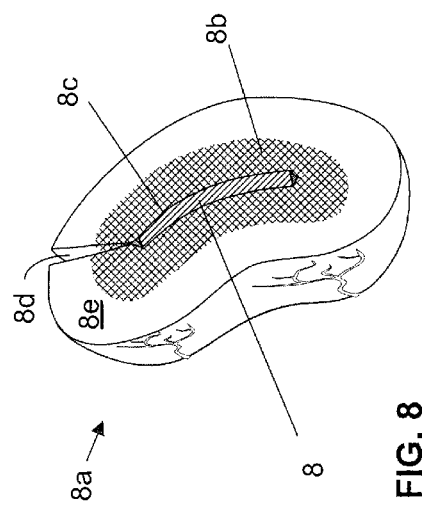
FIG. 8 is a schematic cut-away view of a polymeric radiation-source embedded in diseased tissue for which the source size and geometries are customized, according to an embodiment.

FIG. 8 depicts a cross-section of a customized polymeric radiation-source 8 embedded in diseased organ 8a. The size, shape, and surface geometry polymeric radiation-source 8 is defined by a treatment volume 8b, according to an embodiment.

As shown, organ 8a includes non-diseased tissue 8e and substantially crescent-shaped, diseased tissue defining treatment volume 8b. The size and shape of treatment volume 8b defines in turn the above-noted parameters of the polymeric, radiation-source 8 so that when inserted through incision 8d into treatment volume 8b, a therapeutic dose of radiation permeates to a generally predictable depth through interfacing treatment area 8c into treatment zone 8b thereby minimizing radiation into non-treatment volume 8e of organ 8a.

Figure 10:
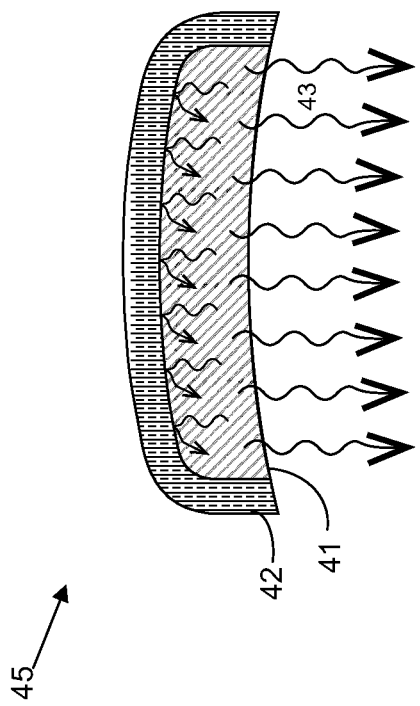
FIGS. 9 and 10 are schematic views of embodiments of a customized, polymeric-radiation-source having both a radioisotope layer and a shielding layer for shielding and directing radiation, according to embodiments.
Figure 9:
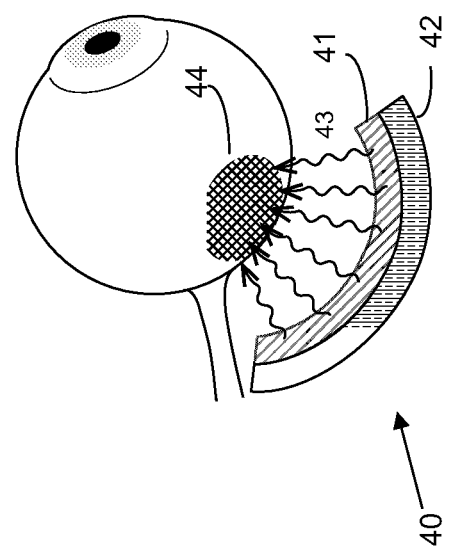

FIGS. 9 and 10 depict composite, polymeric radiation-sources 40 and 45, respectively; each having both a radioisotope layer 41 and a shielding material layer 42, according to embodiments.

As shown in FIG. 9, the general concavity of source 41 directs radiation 43 towards treatment area 44 while shielding material 42 simultaneously contains or reduces outwardly radiating radiation. Suitable shielding materials include heavy metals like, inter alia, gold, platinum, steel, tungsten, lead or non-metallic materials like polymeric materials or fluids; the particular material chosen in accordance with the radiation type being shielded.

As shown in FIG. 10 shielding layer 42 is configured to reflect or focus radiation 43 in the direction the source geometry directs radiation so as to efficiently utilize available radiation capacity of source 41, according to an embodiment. It should be appreciated that in many embodiments composite, polymeric radiation-sources, the shielding material inherently shields and reflects simultaneously. Construction methods described may also be employed to construct composite, polymeric radiation-sources.

Additional applications of embodiments of customized, polymeric radiation source include, inter alia, determining the resolving time of Geiger meter counters, nuclear science instruction with experiments involving radioactivity, and gamma spectroscopy.

It should be appreciated that various combinations of the above-noted features are also included within the scope of the present invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A system for creating and using a customized polymeric radiation-source comprising:
    a device for obtaining image data of a treatment area comprising human tissue with unique contours and irregularities, the image data including shape, volume, and surface geometry data;
    a customized polymeric radiation source formed from an irregular radioactive polymer having a complex of a radioisotope and a bi-functional ligand molecularly bonded with a polymer, the customized polymeric radiation-source matching the unique contours and irregularities of the treatment area in accordance with the image data, the customized polymeric radiation-source having a first thickness; and
    a radiation shielding layer formed adjacent to the customized polymeric radiation-source, the radiation shielding layer having a geometry that mirrors the unique contours and irregularities of the customized polymeric radiation-source, the radiation shielding layer having a second thickness equal to or less than the first thickness of the customized polymeric radiation-source, the radiation shielding layer containing or limiting radiation emitted from the customized polymeric radiation-source.

2. The system of claim 1, wherein the customized polymeric radiation-source matches the volume of treatment area.

3. The system of claim 1, wherein the customized polymeric radiation-source is configured to be positioned in close proximity to the treatment area of human tissue.

4. The system of claim 3, wherein the radiation shielding layer is configured to direct the radiation from the customized polymeric radiation-source towards the treatment area of the human tissue.

5. The system of claim 1, wherein the customized polymeric radiation-source comprises a radioisotope.

6. The system of claim 5, wherein the radioisotope is selected from the group consisting of:
$^{89}$Sr, $^{169}$Yb, $^{90}$Y, $^{192}$Ir, $^{103}$Pd, $^{177}$Lu, $^{149}$Pm, $^{140}$La, $^{153}$Sm, $^{186}$Re, $^{188}$Re, $^{166}$Ho, $^{166}$Dy, $^{137}$Cs, $^{57}$Co, $^{169}$Er, $^{165}$Dy, $^{97}$Ru, $^{193m}$Pt, $^{195m}$Pt, $^{105}$Rh, $^{68}$Ni, $^{67}$Cu, $^{64}$Cu, $^{109}$Cd, $^{111}$Ag, $^{198}$Au, $^{199}$Au, $^{201}$Tl, $^{175}$Yb, $^{47}$Sc, $^{159}$Gd, and $^{212}$Bi.

7. The system of claim 5, wherein the radioisotope is implemented as a particulate radioisotope.

8. The system of claim 5, wherein the at least one radioisotope includes neutron-activated glass.

9. The system of claim 8, wherein the neutron-activated glass is selected from the group consisting of aluminosilicate, magnesium aluminosilicate, and potassium aluminogermanate containing samarium-153, holmium-166, erbium-169, dysprosium-165, rhenium-186, rhenium-188, and yttrium-90.

10. The system of claim 1, wherein the customized polymeric radiation-source includes a radioisotope encased in an at least partially polymeric encasement.

11. The system of claim 10, wherein the radioisotope is selected from the group consisting of:
$^{89}$Sr, $^{90}$Sr, $^{169}$Yb, $^{32}$P, $^{33}$P, $^{90}$Y, $^{192}$Ir, $^{125}$I, $^{131}$I, $^{103}$Pd, $^{177}$Lu, $^{149}$Pm, $^{140}$La, $^{153}$Sm, $^{186}$Re, $^{188}$Re, $^{166}$Ho, $^{166}$Dy, $^{137}$Cs, $^{57}$Co, $^{169}$Er, $^{165}$Dy, $^{97}$Ru, $^{193m}$Pt, $^{195m}$Pt, $^{105}$Rh, $^{68}$Ni, $^{67}$Cu, $^{64}$Cu, $^{109}$Cd, $^{111}$Ag, $^{198}$Au, $^{199}$Au, $^{201}$Tl, $^{175}$Yb, $^{47}$Sc, $^{159}$Gd, and $^{212}$Bi and $^{77}$As.

12. The system claim 1, wherein the customized polymeric radiation-source includes radiation emitters selected from the group consisting of an alpha particle emitter, beta minus and beta plus emitters, Auger electron emitter, gamma-ray emitters, and x-ray emitter.

13. A system for creating and using a customized polymeric radiation-source comprising:
means for obtaining image data of a treatment area comprising human tissue with unique contours and irregularities, the image data including shape, volume, and surface geometry data;

a customized polymeric radiation source formed from an irregular radioactive polymer having a complex of a radioisotope and a bi-functional ligand molecularly bonded with a polymer, the customized polymeric radiation-source matching the unique contours and irregularities of the treatment area in accordance with the image data, the customized polymeric radiation-source having a first thickness; and a radiation shielding layer formed adjacent to the customized polymeric radiation-source, the radiation shielding layer having a geometry that mirrors the unique contours and irregularities of the customized polymeric radiation-source, the radiation shielding layer having a second thickness equal to or less than the first thickness of the customized polymeric radiation-source, the radiation shielding layer containing or limiting radiation emitted from the customized polymeric radiation-source.

14. The system of claim 13, wherein the means for obtaining image data comprises a three dimensional medical imaging device.

15. The system of claim 14, wherein the three dimensional medical imaging device comprises at least one of: a magnetic resonance imaging (MRI) device; three dimensional ultrasound device; a computed axial tomography (CAT or CT) device; and a single-photon emission computed tomography (SPECT) or positron emission tomography (PET) device.

16. The system of claim 13, wherein the customized polymeric radiation-source matches the volume of treatment area.

17. The system of claim 13, wherein the customized polymeric radiation-source is configured to be positioned in close proximity to the treatment area of human tissue.

18. The system of claim 13, wherein the radiation shielding layer is configured to direct the radiation from the customized polymeric radiation-source towards the treatment area of the human tissue.

19. The system of claim 13, wherein the customized polymeric radiation-source comprises a radioisotope.

20. The system of claim 19, wherein the radioisotope is selected from the group consisting of:
$^{89}$Sr, $^{169}$Yb, $^{90}$Y, $^{192}$Ir, $^{103}$Pd, $^{177}$Lu, $^{149}$Pm, $^{140}$La, $^{153}$Sm, $^{186}$Re, $^{188}$Re, $^{166}$Ho, $^{166}$Dy, $^{137}$Cs, $^{57}$Co, $^{169}$Er, $^{165}$Dy, $^{97}$Ru, $^{193m}$Pt, $^{195m}$Pt, $^{105}$Rh, $^{68}$Ni, $^{67}$Cu, $^{64}$Cu, $^{109}$Cd, $^{111}$Ag, $^{198}$Au, $^{199}$Au, $^{201}$Tl, $^{175}$Yb, $^{47}$Sc, $^{159}$Gd, and $^{212}$Bi.

* * * * *